United States Patent [19]

Poot et al.

[11] 4,140,904
[45] Feb. 20, 1979

[54] X-RAY DIFFRACTION APPARATUS

[75] Inventors: Simon Poot, Pijnacker; Wim C. Wuijster, Maasland, both of Netherlands

[73] Assignee: N.V. Verenigde Instrumentenf Abrieken Enrafnonius, Rontgenweg, Netherlands

[21] Appl. No.: 823,863

[22] Filed: Aug. 11, 1977

[30] Foreign Application Priority Data

Aug. 31, 1976 [NL] Netherlands .................. 7609658

[51] Int. Cl.² .......................................... G01N 23/20
[52] U.S. Cl. .................................. 250/272; 250/275
[58] Field of Search ............... 250/272, 273, 274, 275, 250/277 CH

[56] References Cited

U.S. PATENT DOCUMENTS 3,466,438  9/1969  Abrahamsson ...................... 250/275

Primary Examiner—Craig E. Church

Attorney, Agent, or Firm—Haseltine, Lake & Waters

[57] ABSTRACT

An X-ray diffraction apparatus of the kind comprising first and second diaphragm tubes in coaxial alignment, displaceable with respect to each other and defining an adjustable circular diaphragm slit between them, a cylindrical film cassette enclosing the diaphragm slit and provided with a slot for admitting the X-rays, a rotatable specimen spindle enclosed by the first diaphragm tube and an elongated carrier bearing supports for each of the diaphragm tubes at its ends. At least one of the supports is laterally arranged with respect to the associated diaphragm tube and connected with the same by a bridge member having a height slightly smaller than the width of the cassette slot, so that the film cassette may be removed from the apparatus by sliding the cassette slot over the bridge member. In a preferred embodiment, the film cassette performs a reciprocal axial movement and is exclusively supported, during this movement, by the diaphragm tubes.

11 Claims, 6 Drawing Figures

X-RAY DIFFRACTION APPARATUS

BACKGROUND OF THE INVENTION

The invention relates to an X-ray diffraction apparatus for examining a specimen.

A known apparatus of this kind comprises first and second diaphragm tubes in coaxial alignment, which are axially displaceable with respect to each other and define a circular diaphragm slit with an adjustable width between them, a cylindrical film cassette enclosing the diaphragm slit and provided with an axial slot for admitting the X-rays, a collimator for the X-rays arranged outside the film cassette opposite to the cassette slot and the diaphragm slit, a specimen spindle enclosed by the first diaphragm tube on which the specimen to be examined may be mounted opposite to the diaphragm slit, adapted to perform an oscillating or continuous rotation, and an elongated carrier on which supports for each of the diaphragm tubes are arranged near its ends.

Instruments of this kind are frequently used for the examination of crystals, but may also be used for powder radiographs.

In the known instruments of the above-mentioned kind, the diaphragm tubes are completely or substantially completely enclosed by the associated supports. Where an integral film cassette is used, it is consequently impossible to remove the film cassette from the instrument without dismounting one of the diaphragm tubes, in some cases together with the associated support. This is a disadvantage in cases in which a new film must be inserted during a measurement. This disadvantage is aggravated if the examination of the specimen must occur at a prescribed temperature. In such cases, it is usual to keep the specimen at the required temperature by a heat exchange with a cold or hot gas stream, which must be introduced through the second diaphragm tube, since this is the only way through which the specimen is attainable. The gas stream is supplied through a conduit terminating shortly before the specimen and secured to the inside of the second diaphragm tube. As a consequence a removal of the film cassette is only possible by dismounting not only the second diaphragm tube, but also the supply conduit for the gas stream. This is, of course, very laborious, but it also leads to a considerable change of the temperature of the specimen, which causes a discontinuity in the measurement. Examinations in which the temperature of the specimen is not allowed to surpass a certain limit, for instance the melting point, may even be rendered impossible.

It has been proposed to remove the above-mentioned difficulties by the use of a film cassette consisting of two semi-cylinders which are joined when the cassette is inserted in the apparatus. However, the shape of such a cassette is not sufficiently stable, so that the position of the image on the film is not accurately determined. In addition, the position of the image must be measured afterwards on two separate film halves, which leads to a further inaccuracy.

SUMMARY OF THE INVENTION

It is the object of the invention to remove the above-mentioned disadvantages, and to provide an X-ray diffraction apparatus from which the film cassette may be removed in a very simple manner.

According to the invention, at least one of the supports is laterally arranged with respect to the associated diaphragm tube and connected with the same by means of a bridge member of which the height is slightly smaller than the width of the cassette slot, so that the film cassette may be removed from the apparatus by sliding the cassette slot over the bridge member.

In practice, an instrument of the present kind may be used either for a measuring method in which the film cassette is stationary, or for a measuring method in which the film cassette performs a reciprocal axial movement. In the latter case, the reciprocating movement of the film cassette may be provided by a special motor, which is separate from the motor providing the rotational movement of the specimen spindle. The two motors must be synchronized with each other for this purpose, so that it is suitable to make use of step motors.

It is generally preferred, however, to derive the reciprocating movement of the film cassette, together with the rotational movement of the specimen spindle, from a common motor by means of a transmission box, which also constitutes the support for the first diaphragm tube. In a preferred embodiment of the invention, based on this principle, the first diaphragm tube is supported by the transmission box by means of a bridge member, of which the height is slightly smaller than the width of the cassette slot, and which is provided with a bore for admitting a driving shaft for the specimen spindle. For this purpose, the bridge member may connect the transmission box with an internal cylindrical carrier for the first diaphragm tube, and extend through an axial slot of the first diaphragm tube. The driving shaft is preferably coupled with the specimen spindle by means of conical gears with spiral teeth.

The reciprocating movement of the film cassette may be obtained by means of a driving nut adapted to be coupled with the film cassette and displaceable along a screw spindle driven by the common motor and connected with a worm, which is coupled with the driving shaft for the specimen spindle by a worm wheel.

In this case, it is desirable that the coupling between the screw spindle and the driving shaft may be interrupted, so that the specimen spindle may be rapidly turned by hand at the beginning of a measurement, to check whether the specimen is arranged in the right position on the specimen spindle. This may be realized in a simple manner by providing an adjusting nut pressing the worm wheel with a variable force against a flange connected with the driving shaft, so that the coupling between the screw spindle and the driving shaft may be interrupted at will by means of the adjusting nut.

It must also be possible to interrupt the coupling between the driving nut and the film cassette, firstly because it would otherwise be impossible to remove the film cassette, and secondly to enable measurements in which the film cassette is stationary. For this purpose, the film cassette is preferably provided with a displaceable pin, by means of which the coupling may be switched on and off.

In view of the possibility of a gas supply through the second diaphragm tube, it will be preferable in most cases to remove the film cassette from the apparatus on the side of the first diaphragm tube. However, it may also be desirable in certain cases, to remove the film cassette on the other side, i.e. along the second diaphragm tube. For this purpose, the second diaphragm tube may be supported by means of a bridge member of which the height is slightly less than the width of the cassette slot. In a preferred embodiment, this bridge member is secured to the second diaphragm tube and displaceable in a slot of the associated support.

In the known instruments of the above-mentioned kind, the film cassette is mounted on a carriage which is displaceable along one or more rods fixedly arranged in the frame of the apparatus. In view of the removal of the film cassette, it would be very desirable if the carriage could be omitted. This is realized, according to a further aspect of the invention, by an arrangement in which the film cassette slides over the diaphragm tubes and is exclusively carried by the same during its reciprocal movement. In order to reduce the friction to a minimum, it is preferable in this case to provide slide studs on the internal surface of the film cassette, so that the same slides over the diaphragm tubes by means of these studs.

In certain measurements, the specimen spindle must perform an oscillating rotation through a prescribed angle. In the known instruments of the present kind, the arrival of the specimen spindle in the desired end positions is detected by means of switches which are changed over in the end positions. In the instrument according to the invention, the use of such switches would be undesirable, because they would form an obstacle for the removal of the film cassette. This problem may be solved by detecting the arrival at the desired end positions by means of two rings arranged on the specimen spindle outside the first diaphragm tube, and independently adjustable in a circumferential direction. Each of these rings bears a mirror, adapted to reflect the radiation of a fixed radiation source onto a detector. The diameter of the rings is smaller than the internal diameter of the film cassette, so that the same may pass the rings.

DETAILED DESCRIPTION

Figure 1:
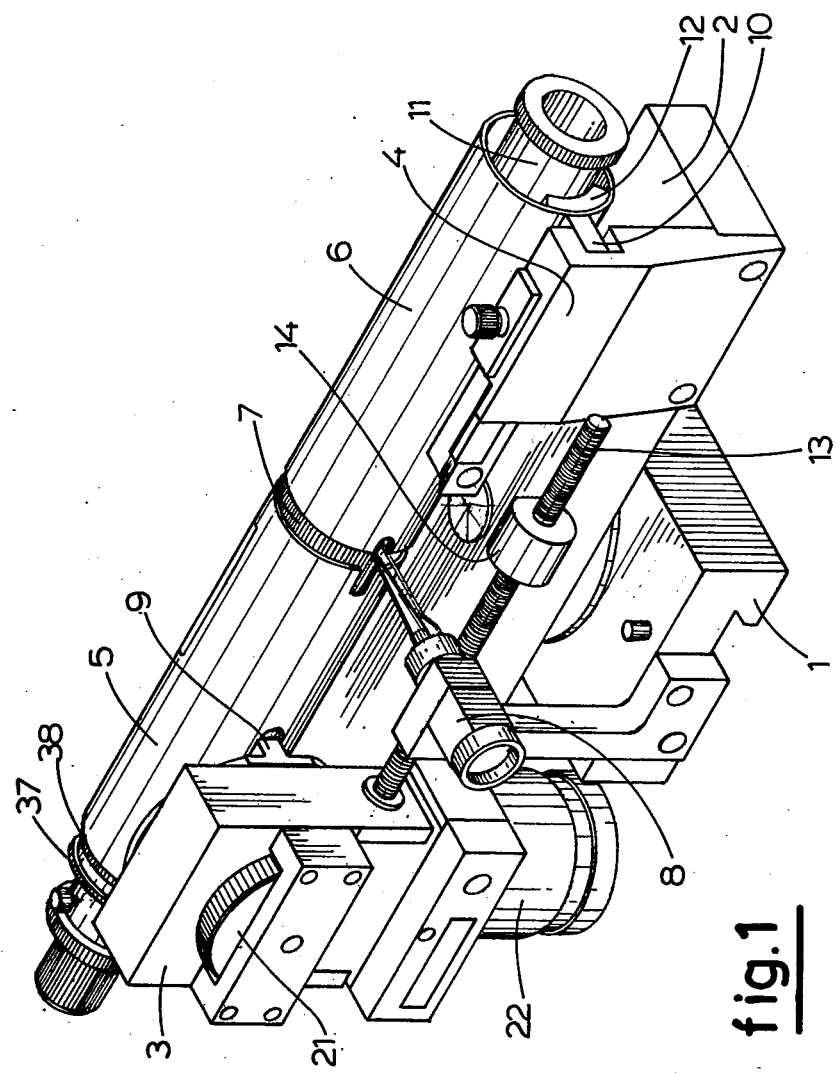
FIG. 1 shows a perspective view of an apparatus according to the invention in which the film cassette has not yet been inserted.

The diffraction apparatus shown in FIG. 1 is carried by a block 1, adapted to be secured to a stand of the usual construction by means of a dovetail connection. An elongated carrier 2 is pivotably mounted on the block 1 and bears a transmission box 3 at one of its ends and a support 4 at its other end.

The apparatus comprises a first diaphragm tube 5 and a second diaphragm tube 6, in coaxial alignment with each other, and mutually displaceable in an axial direction, so that a diaphragm slit 7 with an adjustable width is obtained. A collimator 8 for the X-rays, carried by the block 1, is arranged opposite to the diaphragm slit 7.

The first diaphragm tube 5 is supported by the transmission box 3. For this purpose, the transmission box is provided with a bridge member 9, directed towards the tube 5 and extending through an axial slot of the tube.

The second diaphragm tube 6 is carried by the support 4; for this purpose, the tube 6 is provided with an elongated outwardly directed bridge member 10, which is displaceable in a slot of the support 4. The tube 6 contains an inner tube 11, and a segment-shaped filler 12 has been arranged between the two tubes. The bridge member 10 is secured by means of screws extending through the filler 12 and the wall of the inner tube 11. The tube 11 serves as a holder for expedients for conditioning the specimen, for instance for keeping the specimen at a low temperature.

Contrary to the known constructions, the transmission box 3 and the support 4 are entirely laterally arranged with respect to the diaphragm tubes 5 and 6, so that they do not enclose these tubes.

FIG. 1 also shows a screw spindle 13 which is driven by means of the transmission box 3 and which carries a driving nut 14 for displacing the film cassette.

Figure 2:
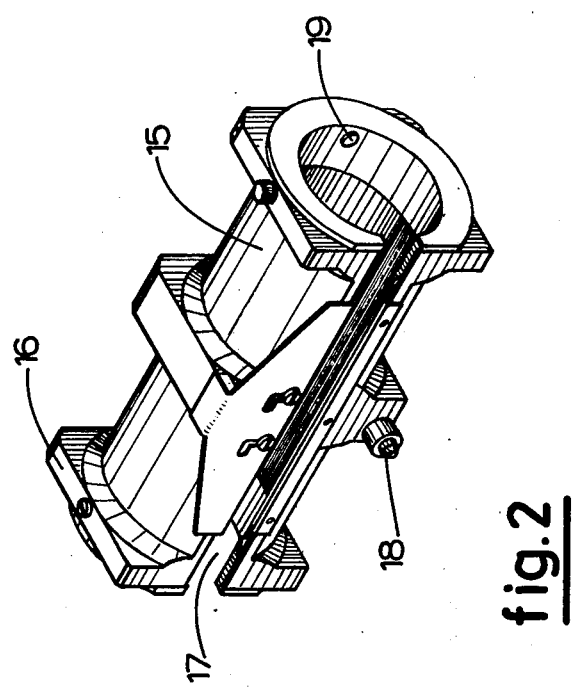
FIG. 2 shows a perspective view of the film cassette to be used.

The film cassette 15 shown in FIG. 2 is carried out in the known manner with a cylindrical shape and with square reinforcing flanges 16. The cassette is provided with an axial slot 17 for admitting the X-rays. During operation, the slot 17 is opposite to the collimator 8. Furthermore, the cassette is provided with a displaceable pin 18 for effecting a coupling with the driving nut 14.

The width of the slot 17 is slightly larger than the height of the bridge members 9 and 10, so that the cassette may be inserted in the apparatus and removed therefrom by sliding the slot 17 over one of the bridge members 9 and 10.

Figure 3:
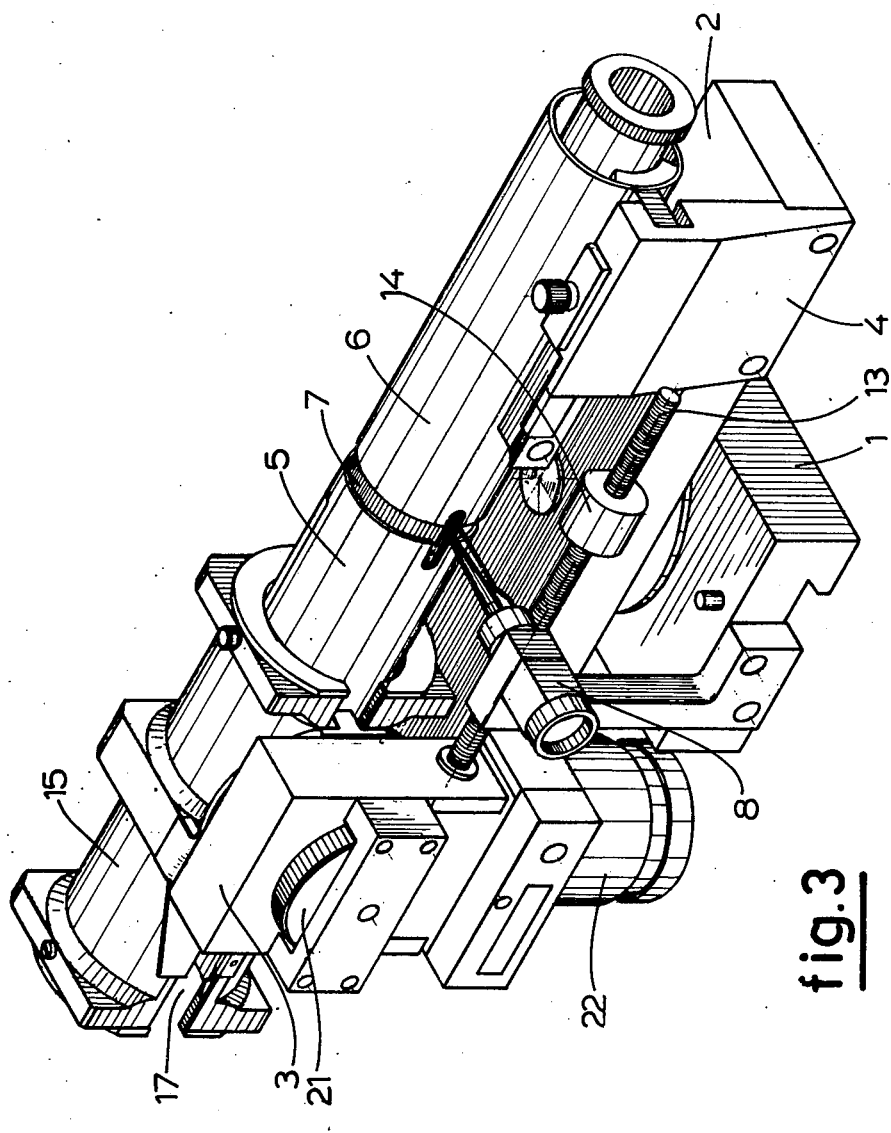
FIG. 3 shows one of the two methods for inserting the film cassette in the apparatus.

FIG. 3 shows how the cassette may be inserted by sliding the slot 17 over the bridge member 9.

Figure 4:
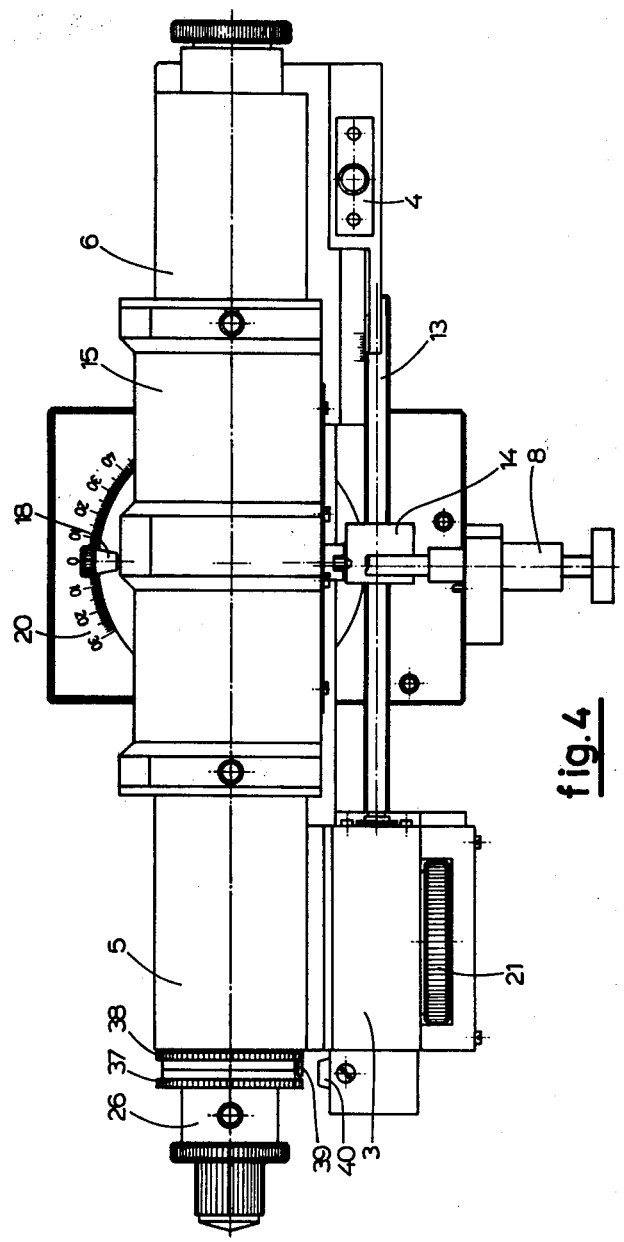
FIG. 4 shows a top view of the apparatus according to FIGS. 1-3 with the film cassette in its operating position.

FIG. 4 shows the operating position of the cassette, opposite to the collimator 8. It also shows how the cassette may be coupled with the driving nut 14 by means of the pin 18.

Contrary to the known diffraction instruments, the cassette 15 is not supported by a carriage during the reciprocating movement obtained by means of the driving nut 14. In fact, the cassette lies on the diaphragm tubes 5 and 6 and is exclusively supported by these tubes. In order to enable a displacement with a low friction, slide studs are provided on the inside of the cassette, for instance three studs equally divided over the circumference at each end of the cassette. The cassette slides over the diaphragm tubes by means of these studs.

FIG. 4 also shows a scale 20, indicating the angular position of the carrier 2 with respect to the block 1.

Furthermore, FIGS. 1, 3 and 4 show an adjusting member 21, by means of which the coupling between the motor and the specimen spindle may be interrupted.

Figure 5:
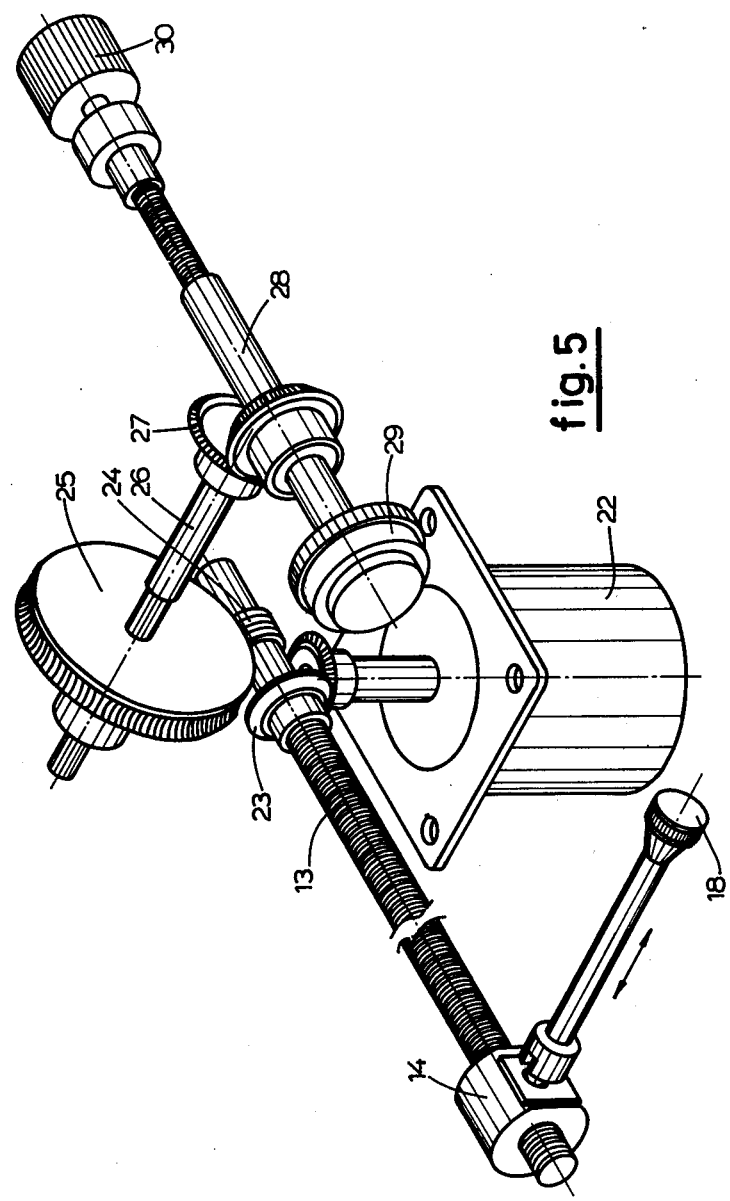
FIG. 5 shows schematically the manner in which the driving nut and the specimen spindle are driven.

FIG. 5 shows schematically the transmission means for driving the specimen spindle and the driving nut. Both movements are obtained by means of a reversible electromotor 22. The motor shaft is coupled with the screw spindle 13 by means of conical gears 23, to that the screw spindle is primarily driven. The movement of the specimen spindle is derived from the rotation of the screw spindle. For this purpose, the screw spindle is connected with a worm 24, engaging a worm wheel 25. The worm wheel 25 is coupled with a driving shaft 26 extending through a bore of the bridge member 9 and coupled, by means of conical gears 27 having spiral teeth, with the specimen spindle 28. The specimen spindle 28 is arranged, in the usual manner, within the first diaphragm tube and bears at one of its ends a fitting 29, on which a goniometer head of known construction may be arranged. The worm wheel 25 may be decoupled from the driving shaft 26. In the decoupled condition, the specimen spindle may be rapidly rotated by hand in order to adjust the required position of the specimen on the spindle in an easy way.

Figure 6:
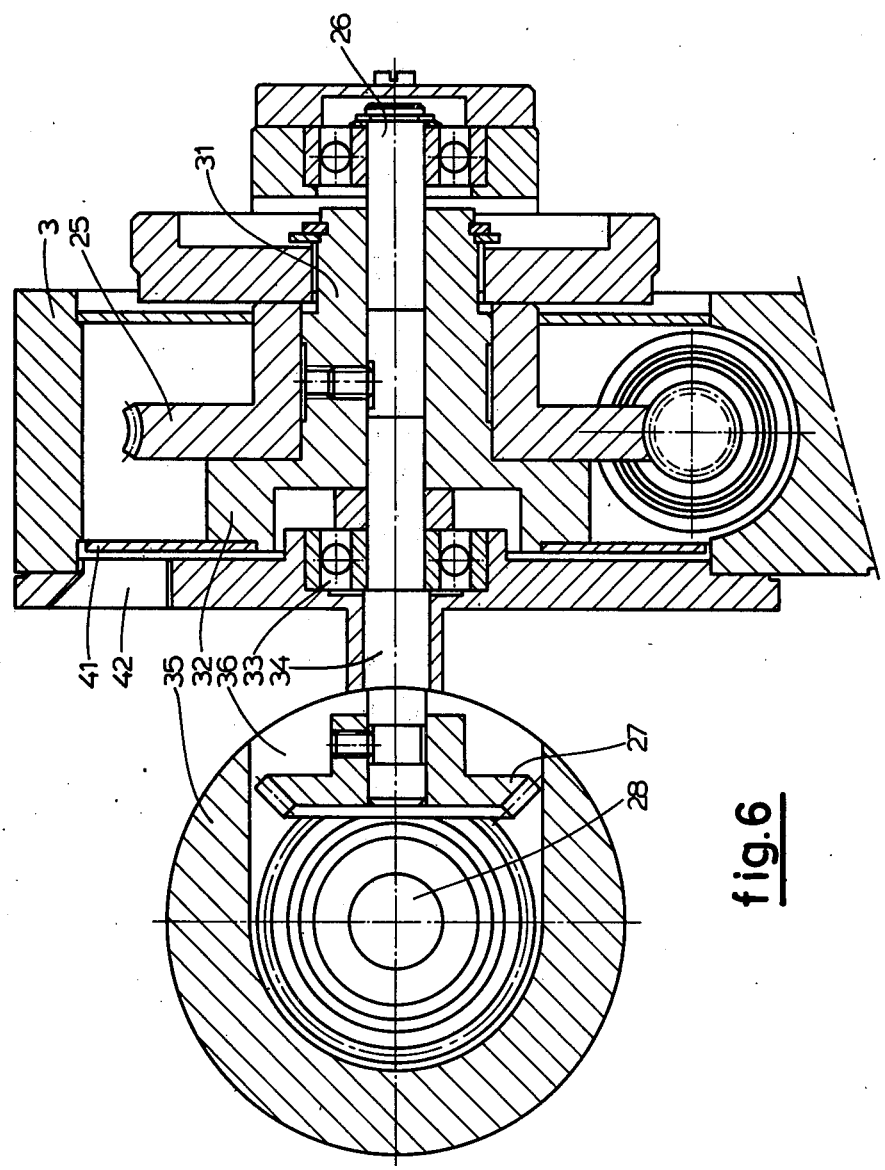
FIG. 6 shows a vertical section of the transmission box of the apparatus according to FIGS. 1-4.

FIG. 6 shows a vertical section of the transmission box 3 along a plane perpendicular to the axis of the diaphragm tube 5. The driving shaft 26 is fixedly connected with a sleeve 31, having an outwardly directed flange 32. The adjusting member 21 is a nut adapted to be adjusted by hand and arranged on the sleeve 31. By means of this nut, the coupling between the worm wheel 25 and the driving shaft 26 may be switched on and off. If the nut 21 is tightened, so that the worm wheel 25 is pressed against the flange 32, the driving shaft is taken along by the worm wheel, so that the specimen spindle is rotated. If the nut 21 is loosened, the driving shaft remains stationary, so that no rotation of the specimen spindle occurs. This decoupling is necessary when the specimen spindle is to be turned by hand by means of the knob 30.

The driving shaft 26 is supported by two bearings 33 and extends through a bore 34 of the bridge member 9. The angular position of the driving shaft with respect to the fixed portion of the apparatus may be read on a disc 41 provided with a graduation and visible through an opening 42.

The first diaphragm tube 5 is supported by a cylindrical supporting body 35, provided with a recess 36 for passing the driving shaft 26, but having a solid structure on both sides of this recess, where it is attached to the bridge member 9 by means of bolts (not shown).

When the specimen spindle 28 and the cassette 15 are coupled with the motor by means of the adjusting member 21 and of the pin 18, respectively, the specimen spindle performs an oscillating rotation and the cassette 15 performs a reciprocating axial movement. The direction of movement is reversed in two final positions which are adjustable by means of rings 37 and 38. The rings 37 and 38 are arranged on a portion of the specimen spindle lying outside the tube 5 and are independently rotatable in a circumferential direction. The diameter of the rings is smaller than the internal diameter of the cassette, so that the cassette may pass the rings. Each of the rings bears a mirror 39, co-operating with a detector head 40 containing a source of infrared radiation and a photodetector. If one of the mirrors stands opposite to the detector head 40, the infrared radiation is reflected onto the photodetector, whereby a signal is generated which causes a reversal of the direction of rotation of the motor 22.

Although the invention has been explained hereinbefore by reference to a measuring method in which the cassette performs a reciprocating movement, the apparatus according to the invention may also be used in measuring methods wherein the cassette remains stationary. In this case, the specimen spindle may either perform an oscillating rotation through a prescribed angle, or a continuous rotation. In the latter case, the optical detector is switched off.

In a measuring method wherein the cassette is stationary, it is possible to use the largest possible portion of the film, if desired, by completely opening the diaphragm slit 7. For this purpose, the tube 6 is moved outwardly through such a distance that the film cassette is only just supported, and the tube 5 is entirely removed. In order to support the other end of the film cassette, an auxiliary ring (not shown) may be placed on the cylindrical supporting body 35.

We claim:

1. An X-ray diffraction apparatus for examining a specimen, comprising a first and a second diaphragm tube in coaxial alignment, which are axially displaceable with respect to each other and define a circular adjustable diaphragm slit between them, a cylindrical film cassette enclosing said diaphragm slit and provided with an axial cassette slot for admitting the X-rays, a collimator for the X-rays arranged outside said film cassette opposite to said cassette slot and said diaphragm slit, a rotatable specimen spindle enclosed by said first diaphragm tube adapted to carry said specimen opposite to said diaphragm slit, an elongated carrier bearing a first support for said first diaphragm tube near one of its ends and a second support for said second diaphragm tube near its other end, at least one of the said supports being laterally arranged with respect to the associated diaphragm tube, and a bridge member connecting said laterally arranged support with the associated diaphragm tube, and having a height slightly smaller than the width of said cassette slot, so that said film cassette may be removed from the apparatus by sliding said cassette slot over said bridge member.

2. Apparatus as claimed in claim 1, futher comprising means for effecting a reciprocating movement of said film cassette, a driving motor, a transmission box constituting said first support and serving to derive said reciprocating movement together with the rotation of said specimen spindle from said driving motor, a first bridge member connecting said transmission box with said first diaphragm tube and having a height slightly smaller than the width of said cassette slot, and a driving shaft for said specimen spindle coupled with said transmission box and extending through a bore of said first bridge member.

3. Apparatus as claimed in claim 2, further comprising a cylindrical carrier inside said first diaphragm tube and connected with said first bridge member, said first bridge member extending through an axial slot of said first diaphragm tube.

4. Apparatus as claimed in claim 2, further comprising a set of conical gears with spiral teeth coupling said driving shaft with sais specimen spindle.

5. Apparatus as claimed in claim 2, further comprising a screw spindle driven by said driving motor, a driving nut displaceable along said screw spindle and adapted to be coupled with said film cassette for effecting said reciprocating movement, a worm secured to said screw spindle, and a worm wheel engaging said worm and coupled with said driving shaft.

6. Apparatus as claimed in claim 5, further comprising a flange connected with said driving shaft, and an adjusting nut pressing said worm wheel with a variable force against said flange, so that the coupling between said screw spindle and said driving shaft may be switched on and off by means of said adjusting nut.

7. Apparatus as claimed in claim 5, further comprising an axially displaceable pin in said film cassette for switching the coupling between said film cassette and said driving nut on and off.

8. Apparatus as claimed in claim 1, further comprising a second bridge member connecting said second support with said second diaphragm tube and having a height slightly smaller than the width of said cassette slot, said second bridge member being secured to said second diaphragm tube and displaceable in a slot of said second support.

9. Apparatus as claimed in claim 2, wherein said film cassette slides over the said diaphragm tubes and is exclusively supported by the same during its reciprocating movement.

10. Apparatus as claimed in claim 9, further comprising a plurality of sliding studs on the inner surface of said film cassette, so that said film cassette slides over the said diaphragm tubes with the said studs.

11. Apparatus as claimed in claim 1, further comprising means for effecting an oscillating rotation of said specimen spindle between two predetermined end positions, two rings having a diameter smaller than the internal diameter of said film cassette, arranged on said specimen spindle outside said first diaphragm tube and independently adjustable in a circumferential direction, a pair of mirrors each borne by one of the said rings, a fixed radiation source, and a detector responding to the radiation of said source, so that the radiation of said source is reflected onto said detector by one of the said mirrors in each of the said end positions to generate a stop signal.